United States Patent [19]
Auhll et al.

[11] Patent Number: 5,207,213
[45] Date of Patent: May 4, 1993

[54] LAPAROSCOPE HAVING MEANS FOR REMOVING IMAGE IMPEDING MATERIAL FROM A DISTAL LENS

[75] Inventors: Richard A. Auhll, Santa Barbara, Calif.; Richard J. O'Hare, Wilton, Conn.; Richard R. Muller, Bronx, N.Y.

[73] Assignee: Circon Corporation, Santa Barbara, Calif.

[21] Appl. No.: 649,544

[22] Filed: Feb. 1, 1991

[51] Int. Cl.$^5$ .............................................. A61B 1/00
[52] U.S. Cl. ............................................ 128/6; 128/4
[58] Field of Search .............................. 128/4, 4 A, 6

[56] References Cited

U.S. PATENT DOCUMENTS

| | | | |
|---|---|---|---|
| 4,741,326 | 5/1988 | Sidall et al. | 128/4 |
| 4,748,970 | 6/1988 | Nakagima | 128/4 A |
| 4,760,838 | 8/1988 | Fukuda | 128/4 A |
| 4,841,951 | 6/1989 | Sato et al. | 128/4 |
| 4,989,581 | 2/1991 | Tamburrino | 128/4 |
| 4,991,565 | 2/1991 | Takahashi | 128/4 |
| 5,020,539 | 6/1991 | Yokoi et al. | 128/4 |
| 5,027,791 | 7/1991 | Takahashi | 128/4 |
| 5,050,585 | 9/1991 | Takahashi | 128/4 |

Primary Examiner—John G. Weiss
Attorney, Agent, or Firm—Daniel J. Meaney, Jr.

[57] ABSTRACT

A laparoscope for performing laparoscopic surgery is shown. The laparoscope includes a rigid elongated sheath tube having a selected length, a distal section and a proximal section. The distal section has a distal tip which includes a fluid tight transparent member, such as a distal lens, which is capable of passing an optical image. The transparent member has an exterior surface located at the distal tip. The laparoscope includes a fluid flow channel which terminates in a nozzle located at the distal tip for directing a fluid flow across the exterior surface of the transparent member to remove image impeding material therefrom such as per example organic material. The laparoscope further includes a first channel which terminates in an orifice which is capable of directing a flow of irrigation fluid along a selected path which, in the preferred embodiment, is a path substantially in alignment with the direction of view of the laparoscope. The laparoscope may optionally include at least one working channel which can be utilized for performing other procedures such as for passing accessories through the laparoscope, to an operating site within the cavity.

A method for performing a laparoscopic procedure in a cavity is also shown. A system for performing a laparoscopic procedure in a cavity is also shown.

57 Claims, 7 Drawing Sheets

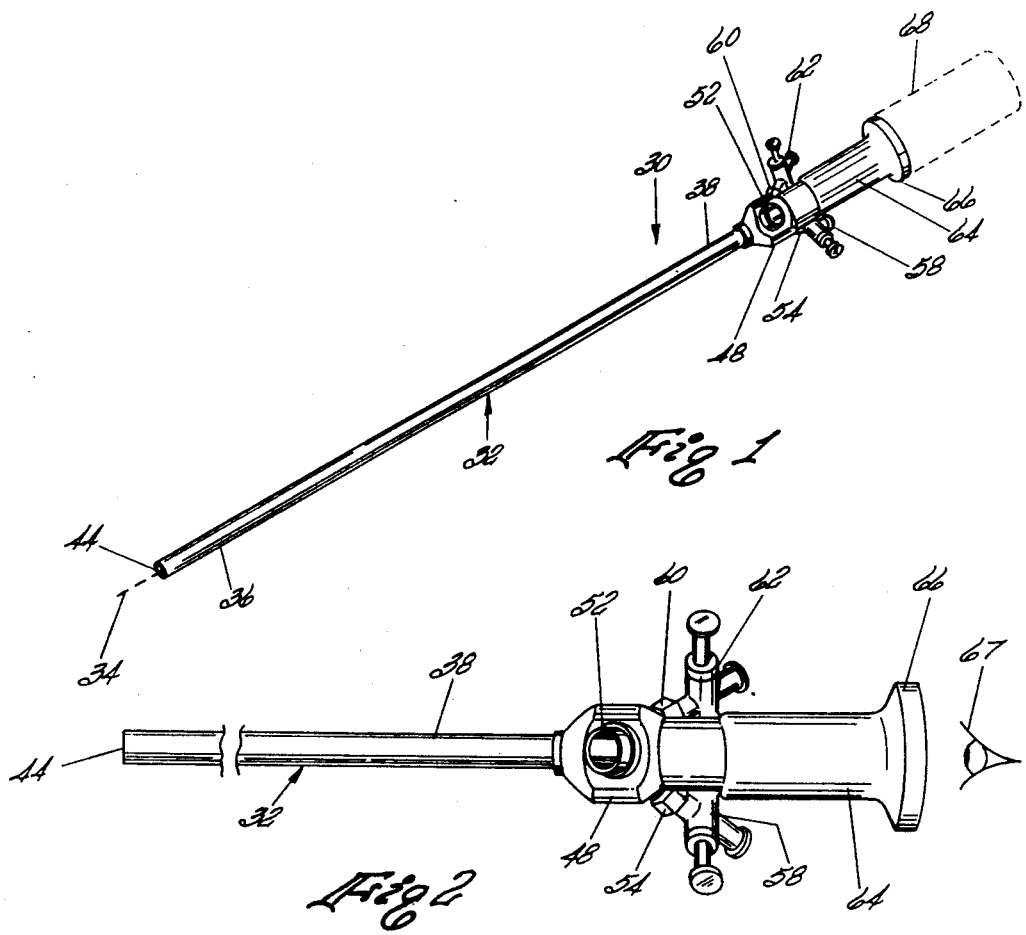
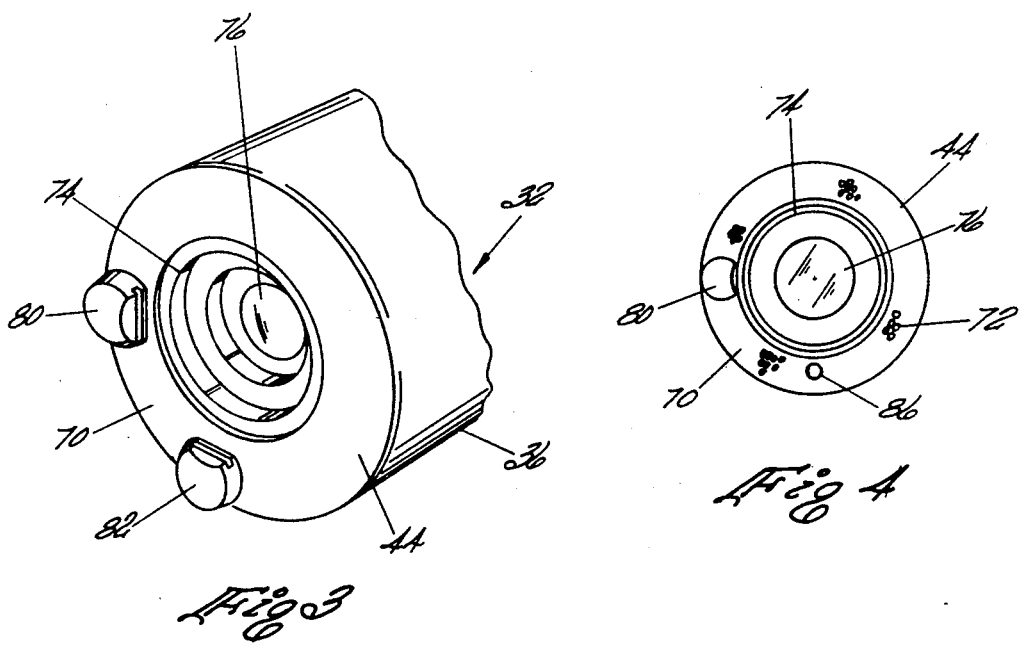

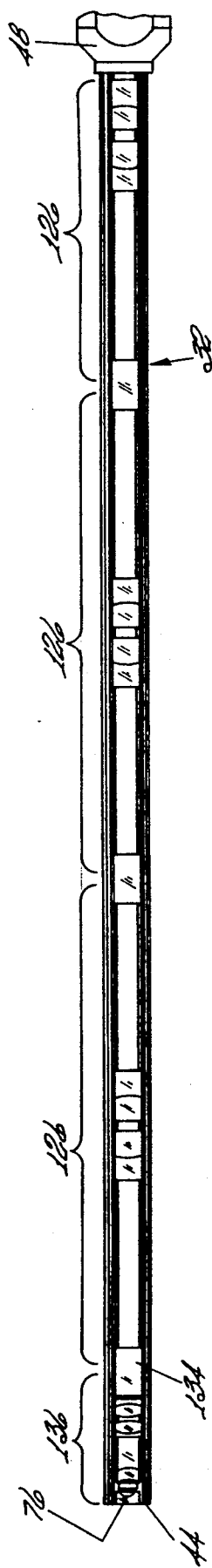
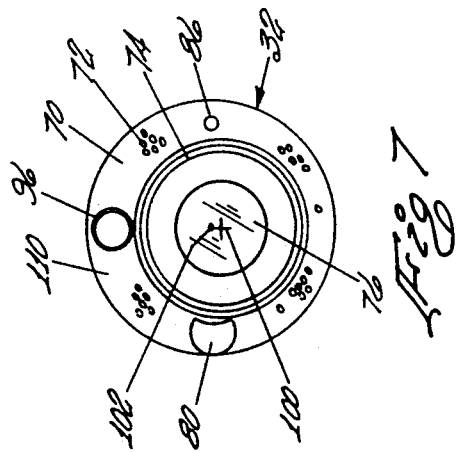
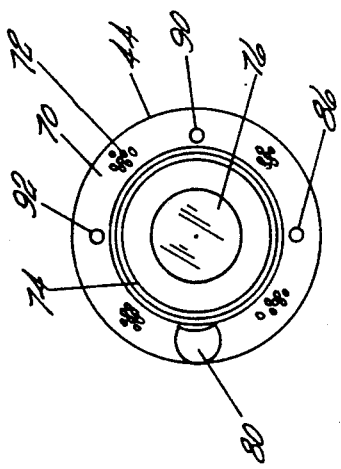
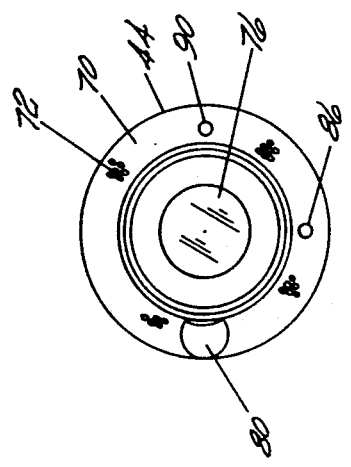

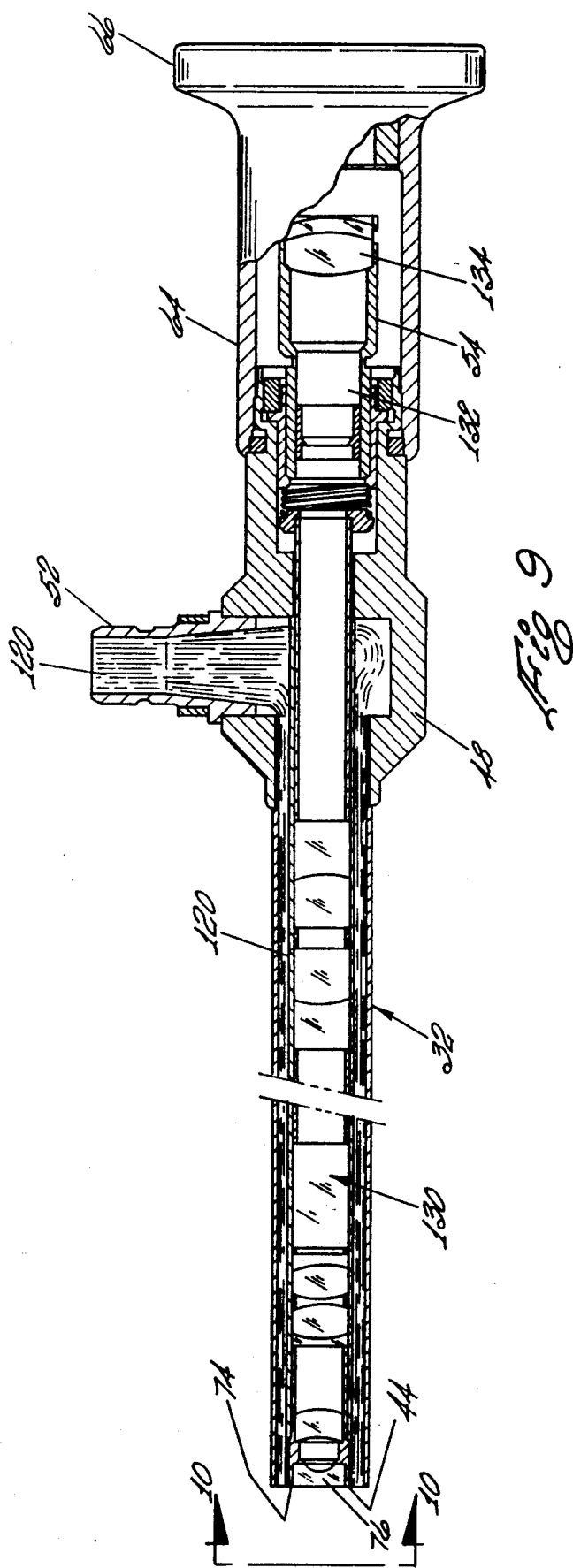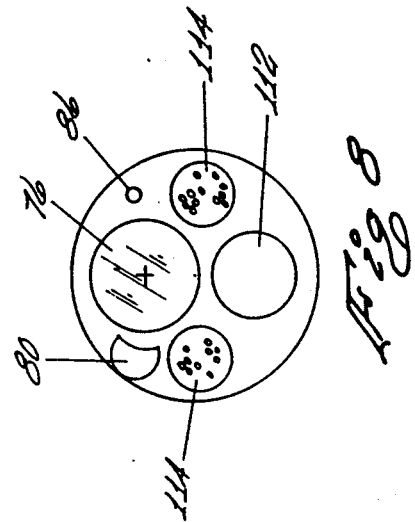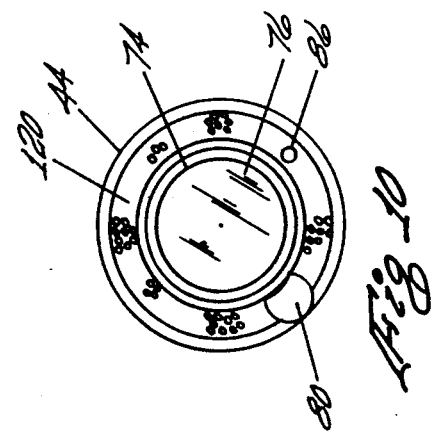

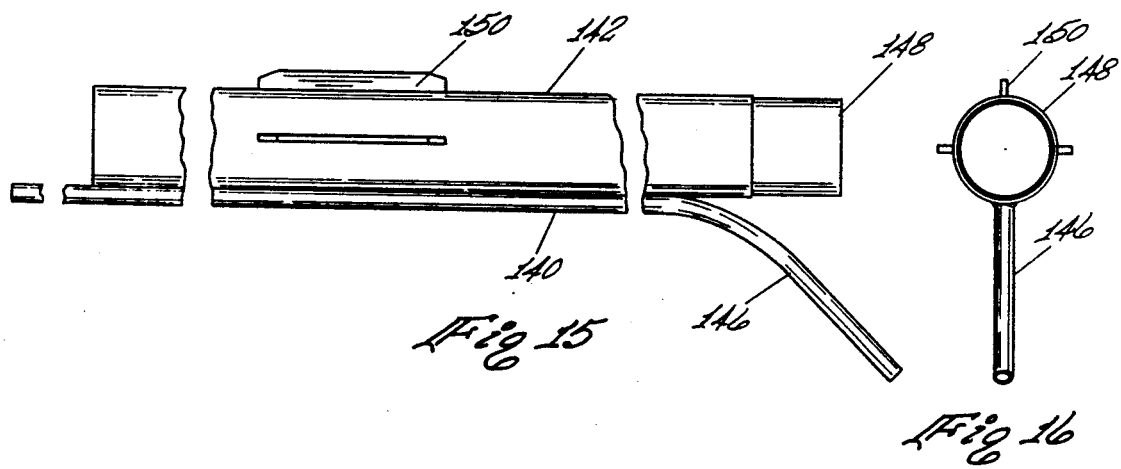
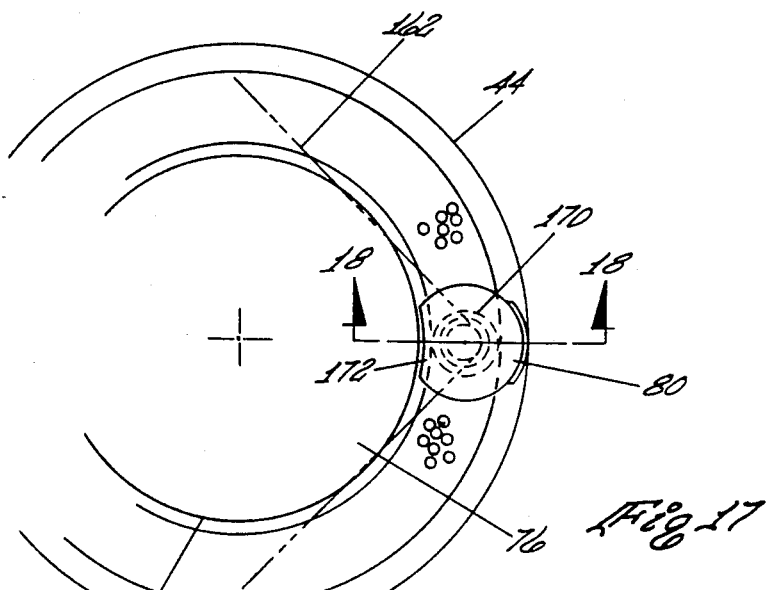
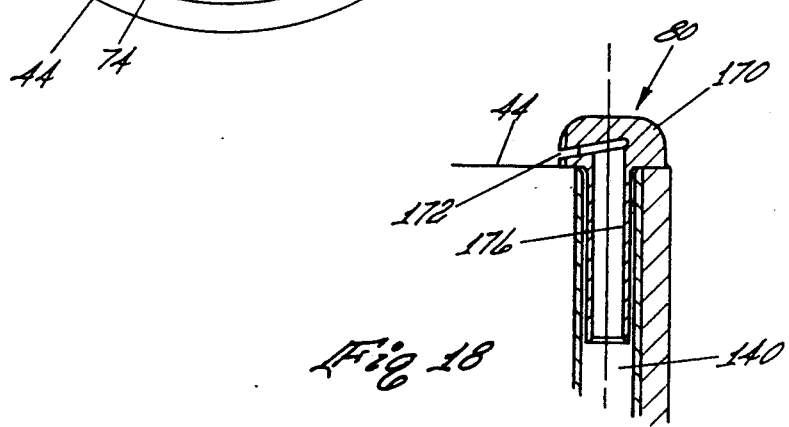

LAPAROSCOPE HAVING MEANS FOR REMOVING IMAGE IMPEDING MATERIAL FROM A DISTAL LENS

BACKGROUND OF THE INVENTION

1. Field of the Invention

This invention relates to a laparoscope which is utilized for performing laparoscopic procedures in a cavity and more particularly is directed to a laparoscope having a distal tip which includes a distal optical lens and a means including a fluid channel for defining a nozzle at the distal tip which is capable of directing a fluid flow across the distal lens to keep the exterior surface free from image impeding material. Additional channels, including an accessory channel, can be provided in the laparoscope to provide a stream of irrigation fluid, for applying suction to a working site or for the passage of working accessories such as laser fibers, electrosurgical probes, bi-polar probes and the like.

2. Description of the Prior Art

The use of laparoscopes for performing laparoscopic procedures is well known in the art. A laparoscope is one class of an endoscope. Endoscopes are used for performing medical surgical procedures. Typically, the state-of-the-art laparoscope includes a rigid elongated sheath tube which encloses a image transferring means channel which receives a fiber optic image light bundle or relay lens system. The image transferring means channel is typically surrounded by fiber optic light carrying means. The distal end of the laparoscope is used to develop an optical image of an operating site within a cavity and the operating site is illuminated by light which is carried to the operating site by the fiber optic light carrying means. The optical image is transmitted through the image transferring means to the proximal end of the laparoscope where a viewable image is observed by the surgeon. The state-of-the-art laparoscopes are usually inserted through a cannula and trocar assembly which makes an incision or opening in the navel or belly-button of a patient. The purpose of making the incision in the navel or belly-button is to minimize the size of the surgical scar which remains upon completion of the surgical procedure. It is also known in the art to utilize a primary cannula and trocar assembly to form the initial opening through the navel or belly-button into the abdomen or the peritoneal cavity and use smaller cannula and trocar assemblies which are inserted into other smaller incisions to provide access to the peritoneal cavity for passing working tools. In the known laparoscopic procedures, the peritoneal cavity is insufflated with an appropriate fluid such as carbon dioxide ($CO_2$) gas, concomitant with laparoscopic or peritoneoscopic examination, diagnosis and/or treatment, including the excision of structures and tissues in the peritoneal cavity. In the recent past, the type of surgeries performed using laparoscopic procedures has been expanded into new minimum invasive surgical procedures. One such new procedure utilizes the laparoscope, with other appropriate instruments, for performing laparoscopic cholecystectomy which is essentially a minimum invasive surgical method for removal of a gallbladder. Similar minimum invasive surgical techniques are being developed using laparoscopes to remove other organs, such as the appendix, kidney or tissues, such as from the liver, also located in the peritoneal cavity.

In the laparoscopic cholecystectomy procedure, the laparoscope is utilized to provide the surgeon with a video image of the operating site. The video image is provided on a color television monitor and that image is used by the surgeon to perform the procedure. To obtain the optical image, a small high sensitivity video camera is usually operatively attached to the eyepiece of the laparoscope. The surgeon is able to insert and manipulate other instruments through auxiliary cannula and trocar assemblies located at small punctures made in the abdomen, all under the view of the surgeon through the video image developed by the video camera.

As part of the laparoscopic cholecystectomy, instruments are utilized through the various small openings to place a traction on the diseased organ. Under observation of the laparoscope, the surgeon attaches clips to the arteries and ducts leading to the gallbladder and then performs an incision between the clips. By using such techniques, the gallbladder is ultimately disattached from the liver. Once the gallbladder has been separated from the liver, the gallbladder can then be pulled through one of the small tiny holes. The patient usually goes home the next day with usually three or four punctures which will form small scars.

The laparoscopic cholecystectomy using a laparoscope is one of the minimum invasive surgical techniques that is expected to be expanded in the future to include other surgical procedures to be performed in the peritoneal cavity and other cavities within the body.

It is also known in the art that when utilizing a laparoscope in a laparoscopic procedure, such as, for example, the laparoscopic cholecystectomy briefly described above, it is necessary that the distal lens be free from light impeding agents such as a layer of fog, protein material or organic material. It is the desire of the surgeon to keep the laparoscope in the peritoneal cavity at all times.

However, it is known that when the distal tip of the laparoscope is inserted into the peritoneal cavity, a fogging occurs across the distal tip which impedes the passage of the optical image and which interferes with the ability of the surgeon to view the operating site. This fogging condition is due to the fact that the operating room temperature is in the order of 20° C. (68° F.). However, the interior of the peritoneal cavity or abdomen is generally at blood temperature which is typically in the order of 37° C. (98.6° F.). Thus, when a laparoscope, which is maintained at room temperature in the operating room which is typically 20° C. has the distal tip thereof at room temperature of about 20° C. inserted into the abdomen having a temperature of approximately 37° C., the temperature differential therebetween is sufficient to cause instant fogging of the distal lens.

One known method for solving this problem art, is to heat the distal tip of the laparoscope by a variety of means. One method that is utilized to heat the distal tip is to insert the distal tip into a container of hot water to raise the temperature of the distal tip to approximately 37° C. Another known technique is to place the distal tip in hot towels to raise the temperature thereof to approximately 37° C.

In addition to the above fogging problem, other image impeding problems are encountered during a procedure. When a surgeon is performing a procedure, that procedure normally results in particulate matter such as protein, blood, tissue and the like, being splattered through the operating site during the procedure. Typically, certain of the particulate matter will adhere to the distal surface and transparent member located at the distal tip of the laparoscope thereby impeding the transmission or passage of the optical image through the transparent member. This is particularly true during use of laser and electrocautery procedures for removing tissue.

In a typical laparoscopic procedure, particulate matter accumulates on the distal end three or four times during a procedure. Each time the optical image is impeded by the accumulation of particulate matter, it is necessary for the surgeon to remove the laparoscope through the cannula and trocar assembly, to physically wipe the particulate matter off of the transparent member, located at the distal tip of the laparoscope, and then reinsert the laparoscope through the cannula and trocar assembly back into the abdominal or peritoneal cavity to continue the procedure.

It is known in the field of endoscopy to utilize endoscopic instruments for performing endoscopic procedures in the upper gastrointestinal tract ("GI Tract"). In performing the endoscopic procedures in the upper GI Tract, the endoscopic procedures are generally performed using flexible instruments such as, for example, a TX-8 panendoscope (Esophago-gastro-duodenoscope) which is one of a family of panendoscopes and other gastro-intestinal endoscopes manufactured by ACMI, a predecessor to the Assignee of the present application.

The TX-8 panendoscope was designed to be used in the upper GI Tract. The TX-8 panendoscope was used primarily as a visualizing instrument and employing flexible optical fibers, both to transmit illumination to the operating site or area immediately in front of the endoscope and to transmit an optical image of that operating site or area from the distal tip to an eyepiece located at the proximal end of the TX-8 panendoscope. The optical image so generated by the TX-8 panendoscope was viewed by an operator or transmitted to a film or television media by means of a television camera.

In the TX-8 flexible panendoscope, Vision or image impeding agents were removed from the front lens and the illumination ports by the use of air, water and suction. The air, water and suction functions were operated by finger controls located conveniently on the control head of the TX-8 panendoscope. The air input also acted as insufflation medium to improve visualization. The suction channel doubled as an end-to-end conduit through which a variety of diagnostic and therapeutic devices, such as forceps, cytology brushes, graspers and the like could be introduced into the field of view to be explored under vision control.

Another known device offered for sale and sold by the predecessor to the assignee of the present invention is a TX-6 Cannulator Duodenoscope which was utilized for endoscopic retrograde cholangio pancreatography. The TX-6 cannulator duodenoscope also included a means for removing image or vision impeding agents from the front lens and irrigation ports of the instrument.

It is also known in the art to utilize a suction-irrigation handle for endoscopic surgery of the paranasal sinuses and the anterior base of the skull. The suction irrigation handle for the endoscope is essentially a rigid sheath which receives a working telescope. The rigid sheath includes a single channel which was capable of being used for either irrigation or suction of the operative site in the paranasal sinuses or in the anterior base of the skull The suction-irrigation handle was utilized by the surgeon to irrigate an operating site with an irrigation solution and then to remove the irrigation solution from the site.

Operating laparoscopes are also known in the art. Typically, the known operating laparoscope has a rigid elongated sheath with a rigid optical path having two prisms, a fiber optic light guide and an operating channel. The operating channel port located at the proximal end of the operating laparoscope is coaxial with the operating channel. The rigid optical path extends perpendicular (at about 90°) from the rigid elongated sheath at the proximal end and then through a 90° bend which then extends the rigid optical path along an axis which is parallel to the axis of the rigid elongated shaft terminating in an eyepiece. Prisms are used at each 90° bend of the optical path. The fiber optic light guide enters the rigid elongated sheath at the proximal end and extends from the proximal end to the distal end. The operating channel was used to pass a monopolar grasping device which was used to perform tubal ligation. Laparoscopes have been known in the art for more than ten years. The fogging of distal tip of laparoscopes has been known for a similar period of time. None of the known prior art discloses, teaches or suggests a solution to the defogging problem. Specifically, none of the prior art laparoscopes include a means within the laparoscope for directing a fluid flow across the exterior surface of an image passing member.

SUMMARY OF THE PRESENT INVENTION

A novel, new and unique laparoscope for performing laparoscopic procedures is disclosed and taught by the present invention. In the preferred embodiment, the laparoscope includes a rigid elongated sheath having a selected length and a distal section. The distal section includes means for defining a distal tip which includes a fluid tight transparent member capable of passing an optical image. The transparent member has an exterior surface located at the distal tip. The laparoscope further includes means located within the rigid elongated sheath tube for defining at the distal tip and nozzle for directing fluid flow, under pressure, across the exterior surface of said transparent member to remove therefrom, optical impeding agents.

None of the known state-of-the-art laparoscopes which include a rigid elongated sheath tube includes means for defogging the distal tip of the laparoscope which occurs due to a temperature differential upon insertion of the distal tip into the abdomen or peritoneal cavity and means for effectively removing particulate matter which accumulates upon the distal tip and distal lens of the laparoscope during a procedure.

In the suction-irrigation handle for endoscopic surgery, the irrigation and suction channel did not include a nozzle for deflecting a fluid flow under pressure across the distal tip of the telescope to remove vision impeding material from or to prevent defogging of the distal tip of the telescope during a procedure.

The laparoscope of the present invention overcomes several of the problems associated with the prior art including both the fogging problem and the foreign and particulate matter problem wherein matter is deposited upon and adheres to the distal end of the laparoscope impeding or inhibiting the passage of the image through the transparent member.

One advantage of the present invention is that the laparoscope can be inserted through a primary cannula and trocar assembly into the peritoneal cavity without the laparoscope immediately fogging at the distal end thereof.

Another advantage of the present invention is that the laparoscope having the irrigation means for applying a fluid flow under pressure across the transparent member through a nozzle does not require preheating or pretreatment of the laparoscope distal tip prior to insertion into the peritoneal cavity.

Another advantage of the present invention is that particulate matter, which may be tissue, protein, blood or the like resulting from the surgical procedure which adheres to or collects upon the distal end of the laparoscope impeding a passage of the optical image through the transparent member can be easily removed during the surgical procedure without interfering with the procedure. This matter can be removed by directing a fluid flow under pressure and through a nozzle across the exterior surface of the transparent member to remove the material from the distal tip and transparent member to permit the surgeon to continue viewing the operative site without the necessity of withdrawing the laparoscope from the cavity during a procedure.

Another advantage of the present invention is that the laparoscope can include an additional one or more working channels and/or an accessory channel which can be utilized for performing additional surgical procedures within the cavity under the direct vision and control of the laparoscope.

Another advantage of the present invention is that the irrigation channel can be utilized for aiming or directing along a predetermined path a fluid flow under pressure, across the tissue or organ subject to the procedure to remove organic material matter therefrom to permit the surgeon to have a clear view during the laparoscopic procedure.

Another advantage of the present invention is that the irrigation channel can be utilized with a high pressure fluid source to perform hydro-dissection of tissue under direct visualization of the laparoscope.

Another advantage of the present invention is that the laparoscope can include one or more working channels of various sizes. The working channels can be of the same size or can be of different sizes. The accessory channels or working channel of the laparoscope can be utilized for performing a plurality of procedures including passage of working tools such as an elongated tube or a laser guide through the channel to the operative site, thereby enabling a surgeon to utilize a laser as part of the operative surgery.

Another advantage of the present invention is that the working channel or accessory channel can be utilized with other probes, such as, for example, a coagulation probe or a BICAP TM electrosurgical probe.

Another advantage of the present invention is that the channel utilized for directing a fluid flow across the exterior surface of the transparent member can be utilized for any type of fluid such as a saline solution or carbon dioxide ($CO_2$) gas. The laparoscope can be structured to have two separate channels, each of which has a nozzle for directing two different type of fluid flows across the exterior surface of the transparent member, such as, for example, a saline solution through one fluid flow channel and a gas fluid through the other channel.

Another advantage of the present invention is that the step of irrigating a working site or the performing of certain procedures which require "triangulation" can be eliminated. Triangulation is required when one or more instruments are inserted into a cavity through different openings and the distal ends of each instrument are direct at appropriate angles to the operative site. Triangulation is usually required to irrigate an operative site by inserting an irrigation tool through one opening and inserting a laparoscope through a second opening. By using the teachings of the present invention in a laparoscope having an irrigation channel or working channels, all channels are in substantial parallel alignment with the elongated axis of the rigid elongated sheath and certain procedures without the triangulation step.

Another advantage of the present invention is a method for performing laparoscopic surgery utilizing the laparoscope of the present invention which includes inserting the laparoscope into the peritoneal cavity, applying a fluid flow across the distal tip of the laparoscope to remove image impeding agents therefrom and for viewing the surgical site through the laparoscope as shown.

Another advantage of the present invention is that a method for performing surgery utilizing the laparoscope of the present invention can include utilizing a laparoscope having an accessory channel or working channel which is capable of passing accessories therethrough for performing surgical procedures under direct visualization of the laparoscope. During the procedure, as impeding agents, such as protein material, tissue material or the like is deposited upon the distal lens, by use of the distal nozzle for directing a fluid flow across the exterior surface of the transparent member, the surgeon can perform the entire laparoscopic procedure without removing the instrument therefrom until the completion of the surgery.

Another advantage of the present invention is that the method for performing laparoscopic surgery utilizing a laparoscope having the distal nozzle fluid flow washing means of the present invention, can perform the surgical procedure more efficiently without the requirement that the laparoscope be removed from the peritoneal cavity during the procedure thereby decreasing the time required for a surgeon to complete a procedure.

Another advantage of the present invention is that the laparoscope having a distal nozzle and working and/or accessories channels can form part of a system for performing laparoscopic procedures.

BRIEF DESCRIPTION OF THE DRAWINGS

These and other advantages of the invention will be readily apparent when considered in light of the detailed description hereinafter of the preferred embodiment and of the drawings which include the following figures:

FIG. 1 is a top and front perspective view of a laparoscope for practicing this invention and include an elongated tube which could be extended beyond the distal end of the laparoscope;

FIG. 2 is a partial top plan sectional view showing the proximal end of a laparoscope for practicing this invention;

FIG. 3 is a distal section perspective view of one embodiment of the laparoscope of FIG. 1 showing a distal tip having a transparent member for passing an optical image and two nozzles for directing different fluid flows across the exterior surface of the transparent member;

FIG. 4 is a distal end elevational view showing another embodiment of a laparoscope having a single nozzle for directing a fluid flow across the exterior surface of a transparent member and a means for defining an orifice for directing a stream of irrigation fluid along a predetermined path to a working site to irrigate the same;

FIG. 5 is a distal end elevational view of yet another embodiment of FIG. 4 showing an additional working channel;

FIG. 6 is a distal end elevational view showing yet another embodiment of FIG. 5 having a fourth channel;

FIG. 7 is a distal end elevational view of yet another embodiment of a laparoscope of the present invention having a nozzle, an irrigation flow orifice, which could be utilized as a first working channel, and an accessory or working channel which is larger than the first channel, and which is adapted to pass working accessories;

FIG. 8 is another embodiment of a laparoscope having the fluid flow channel and nozzle, irrigation flow channel, two working channels, an image transferring means and a bifurcated fiber optic light guide means;

FIG. 9 is a partial cross-sectional front elevational view showing the optical components of the preferred embodiment of a laparoscope for practicing this invention;

FIG. 10 is a distal end view of the laparoscope of FIG. 9;

FIG. 11 is a front partial cross-sectional view showing a lens relay system which is one embodiment of an image transferring means;

FIG. 15 is a partial front View of a sub-assembly formed of an image transferring means channel having a fluid flow channel which is operatively connected to and which extends from the proximal end to the distal end of the laparoscope;

FIG. 16 is a right end elevational view of the image transferring means channel and fluid flow channel sub-assembly of FIG. 15;

FIG. 17 is a pictorial representation of the distal end of the laparoscope showing the relationship between the nozzle and the distal lens and the angle of discharge from the nozzle;

FIG. 18 is a partial cross-sectional view of the nozzle position positioned within the fluid flow channel taken along section of lines 18—18 of FIG. 17;

DESCRIPTION OF THE PREFERRED EMBODIMENT

Figure 12:
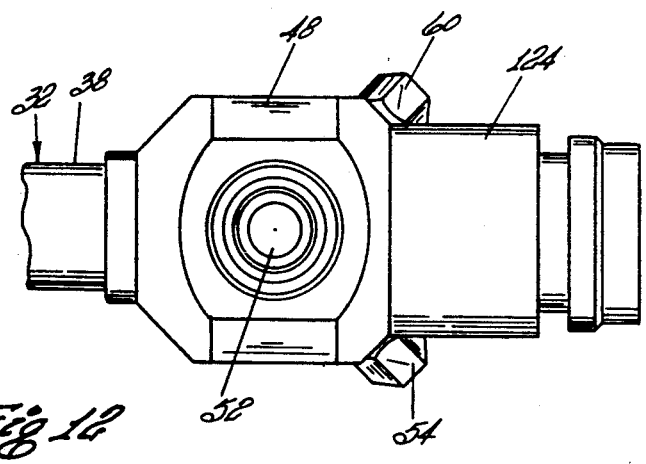
FIG. 12 is a partial top elevational view of an extension member which is operatively connected to the proximal end of the rigid elongated sheath tube of a laparoscope and wherein the extension member includes means for receiving a valve means.

FIG. 1 illustrates an instrument, shown generally as 30 which, in the preferred embodiment is a laparoscope, for practicing the present invention. The instrument 30 includes a rigid elongated sheath tube 32 having a selected length and a distal section or end 36 and a proximal section or end 38. The distal end 36 terminates in a distal tip shown generally as 44. The interior of the laparoscope includes image transferring means for transferring an image from the distal tip 44 through the rigid elongated sheath tube 32 to the proximal end 38 of the laparoscope. The proximal end 38 of the laparoscope is operatively connected to an extension member shown generally as 48. The extension member 48 includes means for supporting a light post 52 and means for defining openings or ports for two channels, which openings are shown as 54 and 60 (60 being visible in FIG. 2). Valve means, which in the preferred embodiment are trumpet valves 58 and 62, are operatively connected to openings 54 and 60, respectively. An eyepiece housing, shown generally as 64, terminates in an eyepiece 66 which permits a surgeon to view the optical image transferred through the laparoscope. Also, it is well known in the art that a video camera 68, which is shown by dashed lines, can be operatively connected to the eyepiece 66 to convert the optical image into a video signal which is ultimately processed by a video processing means to produce a video image on a monitor or video signals for storage of the video image on magnetic tape or other storage means.

The laparoscope 30 may include a plurality of channels which can be used for a number of functions Several species of laparoscopes are disclosed herein. It is envisioned that a laparoscope of the present invention could include a working or accessory channel having a dimension sufficient to pass an elongated tube which could extend beyond the distal end 44 and such extended tube is depicted by dashed line 34. The elongated tube could be used for a number of functions. For example, the elongated tube depicted by dashed line 34 could be used for suction. The end of the elongated tube could be placed into fluid adjacent the distal end 46 while keeping the distal end 44 away from the fluid and enabling the user to view the operating site.

Also, in certain instances, the elongated tube depicted by dashed line 34 could be used to pass working accessories such as, for example, a laser guide. The elongated tube could be extended manually or the laparoscope could include a means for extending the elongated tube.

FIG. 2 shows in greater detail the structure of the extension member 48 and the relationship between the means for defining openings 54 and 60, the trumpet valves 58 and 62 and the relationship therebetween to the eyepiece housing 64. Also, an eye is depicted as 67 to enable a user to view an image through the eyepiece 66.

FIG. 3 shows one embodiment of a distal end of a laparoscope utilizing the teachings of the present invention. In the embodiment of FIG. 3, the distal tip 44 includes means which are located within the rigid elongated sheath tube 32 for defining at the distal end 36 a means for directing a fluid flow across the exterior surface of an image passing means shown generally as 76. Image passing means 76 is located in the center of an aperture 74. In FIG. 3, the image passing means may be a distal lens, a window for a charge coupled device, window for a video sensor or the like. A laparoscope having a video sensor located at its distal end may be known as a videolaparoscope. In FIG. 3, the means for directing a fluid flow across the exterior surface is shown generally as nozzle 80. Nozzle 80 is operatively connected to a means for forming a fluid flow channel which extends from the distal tip 44 of the laparoscope to the proximal end of the elongated sheath tube 32. The nozzle 80 is designed to direct the fluid flow in a wedge-shaped flow pattern and at an angle substantially normal to the axis of the rigid elongated sheath tube 32. The nozzle 80 is located in a space shown as 70 which houses a fiber optic light guide means which is discussed in greater detail in FIGS. 8 and 9.

In the embodiment of FIG. 3, a second channel may be used as a fluid flow channel and terminates in a second nozzle 82. In the embodiment of FIG. 3, the nozzle 80 can be utilized for one type of fluid flow, such as, for example, a saline solution under a pressure of approximately 300 millimeters of Hg.

The pressure range could be in the order of about 200 millimeters of Hg to about 350 millimeters of Hg with about 300 millimeters of Hg being preferred. The lower the pressure, the less cleansing action occurs. The fluid could be any appropriate solution other than a saline solution. Use of pressures greater than 350 millimeters of Hg. could be used depending on the procedure.

The second nozzle 82 can be operatively connected to an alternate source of fluid, such as, for example, a carbon dioxide ($CO_2$) gas. The surgeon, by use of the appropriate valve means, can selectively direct a flow of saline through nozzle 80 or a flow of gas through nozzle 82 across the exterior surface of the image passing means 76 to remove image impeding agents therefrom. In the embodiment of FIG. 3, the image passing means is in the form of a transparent member 76 which is adapted to pass an optical image therethrough to an image transferring means which transfers the image to the proximal end 38 of the laparoscope where the image is received by an eyepiece 66. At the eyepiece 66, the image is directly viewable by a surgeon, or the image can be utilized as an optical image input to a video camera, shown as 68 in FIG. 1.

The embodiment of FIG. 3 is an alternative embodiment. The embodiments of FIGS. 4 through 7 are the preferred embodiments.

FIG. 4 illustrates yet another embodiment of a laparoscope having a nozzle and an irrigation channel. Specifically, the distal end 44 of the laparoscope includes a transparent member 76 which is located in an apertured opening 74. In FIG. 4, the nozzle 80 which is located in the space 70, directs a fluid flow across the exterior surface of the transparent member 76. A second channel 86 terminates in a means defining an orifice for directing a stream of fluid along a predetermined path which, in the preferred embodiment, is substantially along a path which is in axial alignment with elongated axis of the rigid elongated sheath tube 32. The means defining an orifice can be a conical or tapered shaped nozzle or other shaped nozzle to control the characteristics of the irrigation stream. Space to provide a passageway for fiber optic elements as depicted by elements 72 to form a light guide to illuminate the operative site.

FIG. 5 shows yet another embodiment of a laparoscope using the teachings of the present invention. In FIG. 5, the distal end 44 of the laparoscope includes a nozzle 80 and an irrigation channel 86 as described above in connection with FIG. 4. In addition, a third channel shown as 90 is likewise located in the space 70 which extends between the transparent member 76 and the rigid elongated sheath tube 32. In the embodiment of FIG. 5, the fluid flow channel terminating in nozzle 80, the irrigation flow channel 86 and the third channel 90 are positioned at approximately a 90° angle from each other. The axis of the image transferring means which terminates adjacent the transparent member 76 is in coaxial alignment with the elongated axis of the rigid elongated sheath tube 32. The third channel 90 can be used as a working channel to introduce operative probes and devices to the surgical site.

FIG. 6 is yet another embodiment of the present invention which is essentially the embodiment of FIG. 5 with a fourth channel 92, which channel 92 can be utilized as a second working channel. In the embodiment of FIG. 6, the fluid flow channel which terminates in nozzle 80, the irrigation fluid channel 86, and the third channel 90 and the fourth channel 92 are equally spaced around an image transferring means which in the preferred embodiment is a transparent member 76.

Also, the axis of the transparent member 76, is in coaxial alignment with the elongated axis of the rigid elongated sheath tube 32. In the embodiment of FIG. 6, the third channel 90 and the fourth channel 92, have the same dimensions. Further, the dimension of the irrigation fluid flow channel 86 and the third channel 90 are selected to be of the same dimension in this embodiment. However, it is envisioned that the dimension of the irrigation channel and third channel could be of different dimensions.

FIG. 7 illustrates yet another embodiment of a laparoscope utilizing the teaching of the present invention. The distal end 44 of the laparoscope has a different structure than that of the structure of FIGS. 4 through 6. One difference is that the transparent member 76 has its axis 100 offset relative to the elongated axis 102 of the rigid elongated sheath tube 32. As such, the apertured opening 74 is off center relative to the elongated axis 102 but is in coaxial alignment with the central axis 100 of the transparent member 76. As a result of the offset of the axis 100 and 102, an expanded space shown generally as 110 is provided between the rigid elongated sheath tube 32 and the image transferring means channel located within the laparoscope. One structure for an image transferring means channel is described in greater detail in FIGS. 8 and 10.

In FIG. 7, the nozzle 80 is positioned to direct a fluid flow over the exterior surface of the transparent member 76. The irrigation flow channel 86 is located in a different position relative to its position illustrated in FIGS. 4, 5 and 6. In this embodiment, channel 86 is in an opposed spaced relationship to the fluid flow channel, which terminates in the nozzle 80. In the expanded space 110, a working channel 96 is provided to handle special applications, such as, for example, passage of a laser fiber guide, a electrocautery probe, a BICAP TM probe or an elongated tube.

As is illustrated in FIG. 7, the geometric dimension of the accessory channel 96 is substantially greater than the geometric dimension of the irrigation channel 86. A fiber optic light guide means is interspersed in space 70 and expanded space 110 and around the fluid flow channel which terminates in nozzle 80, the irrigation channel 86 and the working channel 96.

In the preferred embodiment of FIG. 7, the outside dimension of the laparoscope having a circular cross-section is about 10 millimeters (about 0.394 inches). The term "generally rounded cross-section" is intended to cover a circular cross-section or elliptical cross-section or the like. The inside diameter of the fluid flow channel is about 1 millimeter (about 0.039 inches). The inside diameter of the working channel has an inside diameter of about 2 millimeters (about 0.080 inches). The image transferring channel has an inside diameter of about 6.0 millimeters (about 0.240 inches) and an outside diameter of about 6.5 millimeters (about 260 inches). The selected length of the rigid elongated sheath tube can range between about 150 millimeter (6 inches) to about 350 millimeters (about 14 inches) with the preferred length to be about 300 millimeters (about 12 inches). It is envisioned that the cross-sectional shape of a laparoscope could be other than a circular cross-section. For example, the cross-section could be elliptically shaped, triangular shaped of the like. The exterior geometrical dimension of the rigid elongated sheath tube could be in the range of about 5 millimeters to about 15 millimeters with about 10 millimeters being preferred.

FIG. 8 is another embodiment of the laparoscope of the present invention wherein the distal end 44 including a nozzle 80, is located at the distal end of the fluid flow channel. In addition, an irrigation channel 86 is positioned adjacent the transparent member or distal lens 76. The operating channel 112, which may be an operating channel having a diameter in the order of 1.5 millimeters to 3 millimeters, is located below the distal lens 76. The illumination for the operating site is provided by a bifurcated fiber optic light bundle 114. In the embodiment, the laparoscope provides a fairly uniform illumination of the operating site while providing a working channel which can accommodate working tools or accessories, laser guides and the like requiring a channel of about 1.5 millimeters to 3 millimeters in dimension. In the preferred embodiment, the working channel is about 1.5 millimeters.

In the event that the working channel or accessory channel is to be used as an aspirator, a suction tube or aspirator probe could be used. The outside diameter of such a suction tube or aspirator probe would be selected to be a dimension to enable the tool to be passed through the working channel and to enable the end thereof to extend a selected distance beyond the distal end of the laparoscope and into the fluid to be aspirated.

Typically, the outside diameter of an aspirator probe is in the order of about 2.5 millimeters. FIG. 1 illustrates an elongated tube shown by dashed line 34 which may be an aspirator probe.

FIG. 9 illustrates in greater detail, the internal structure of the laparoscope for the present invention. In FIG. 9, the rigid elongated sheath tube 32 terminates in an apertured opening 74 which has the transparent member 76 positioned centrally therein. Thus, the distal end 44 is defined by the apertured opening 74 and the transparent member 76. A fiber optic light guide 120 extends from a light post 52 through the extension tube 48 and then is interspersed around the image transferring means channel shown generally as 130. In FIG. 9, a fluid flow channel and other channels are not shown, but the positions thereof are shown in FIG. 10.

Referring again to FIG. 9, the image transferring means shown generally as 130 terminates in a field lens 132 which is located within the eyepiece housing 64. The image is then passed to an ocular lens 134 and through the eyepiece 66.

FIG. 10 shows the distal end 44 of the laparoscope of FIG. 9. The fluid flow channel which terminates in nozzle 80 and the irrigation channel 86 are shown. The fiber optic light carrying means 120 is interspersed in space 70 around the channels.

FIG. 11 depicts a laparoscope showing in greater detail one embodiment of a lens element image transferring means. In the embodiment of FIG. 11, the rigid elongated sheath tube 32 encloses a lens element image transferring system which comprises three relay stages shown generally as 126. Each relay stage includes a pair of lenses and a field lens. Each of the relay stages 126 are positioned to be in axial alignment with its adjacent lens relay stage. At the distal end of the laparoscope, an objective lens system 136 (which may include other lenses) and a field lens 134 are provided to receive and transfer an optical image from the transparent member 76 located in the apertured opening 74 to the relay lens system. In the embodiment of FIG. 11, the central axis of the transparent member 76 is in axial alignment with the axis of the lens element image transferring means including the objective lens 136 and the field lens 134.

The objective lens 136 could include a prism or an optical shaped wedge located distal to the objective lens at the distal tip to provide a deviated direction of view having an angle of about 0° to about 45° and with a range of about 0° to 30° being preferred when viewing in air or $CO_2$. Alternatively, the objective lens system 136 could incorporate a prism to deviate the optical axis to some angle which is oblique to the elongated sheath tube axis. Such deviating prism objectives are common in the endoscopic art, and are commonly available for laparoscopes of viewing angles of 30° and 45°.

The proximal end of the image transferring means terminates in a field lens and an ocular lens system which, in turn, transfers the image to the eyepiece as described above in connection with FIG. 9.

Lens element image transferring means and coherent fiber optic image transferring means are well known to a person skilled in the art and need not be described in greater detail herein.

The image transferring means could include a rigid cane-like or etched fiber optic image bundle in lieu of the lens element relay image transferring system. Any type of image transferring means can be used in practicing this invention. Also, the transparent member 76 can be a window, or could be an exterior surface of a lens element, as depicted in FIG. 11 or could be the distal surface of a prism or of an optical shaped wedge. The term "transparent member" is intended to apply to any exterior surface of an image transferring element which defines a portion of the distal surface of the distal tip 44. In the preferred embodiment, the transparent element may be a window formed of sapphire.

FIG. 12 depicts in greater detail, the structure of the extension member 48 in its relationship to the rigid elongated sheath tube 32. Specifically, the proximal end 38 of the rigid elongated sheath tube 32 is operatively connected to the extension member 48. A light post 52 is positioned to be operatively attached to the extension member 48. The fiber optic light guide means is located in light post 52 and is interspersed within the laparoscope as described in connection with FIG. 14. In the embodiment illustrated in FIG. 12, the light post 52 is depicted to extend normally from the extension member 48. However, it is envisioned that the light post 52 could take other physical shapes, such as, for example, the light post 52 could be in the form of an elbow having a 90° deflection and which extends in a direction towards the upper housing section 124.

Also, the means for defining opening or ports 54 and 60 for the fluid flow channel and the irrigation channel, respectively, are operatively connected to the extension member 48. The upper portion 124 of the extension member 48 is adapted to be operatively connected to an eyepiece 66 as depicted in FIG. 1 or to any other type of optical image receiving means such as, for example, a video camera.

Figure 14:
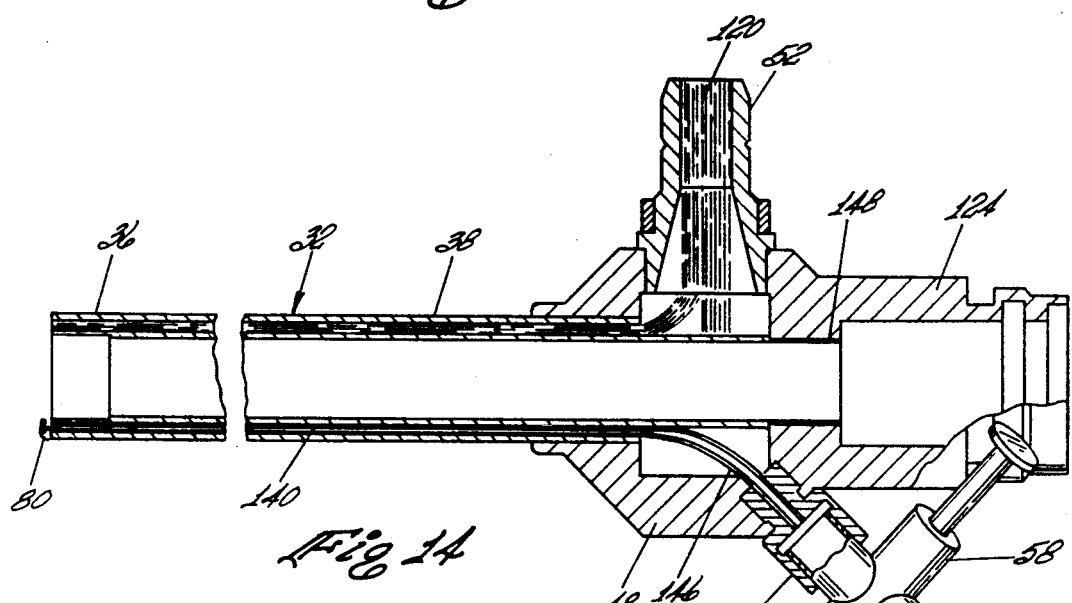
FIG. 14 is a partial cross-sectional side elevational view taken along section lines 14—14 of FIG. 13 showing an extended housing section of the extension member which operatively attached to the proximal end of the rigid elongated sheath tube and showing the relationship between a light post and a means for defining an opening which is operatively connected to a fluid flow channel and valve means which terminates in a nozzle at the distal end of the laparoscope.
Figure 13:
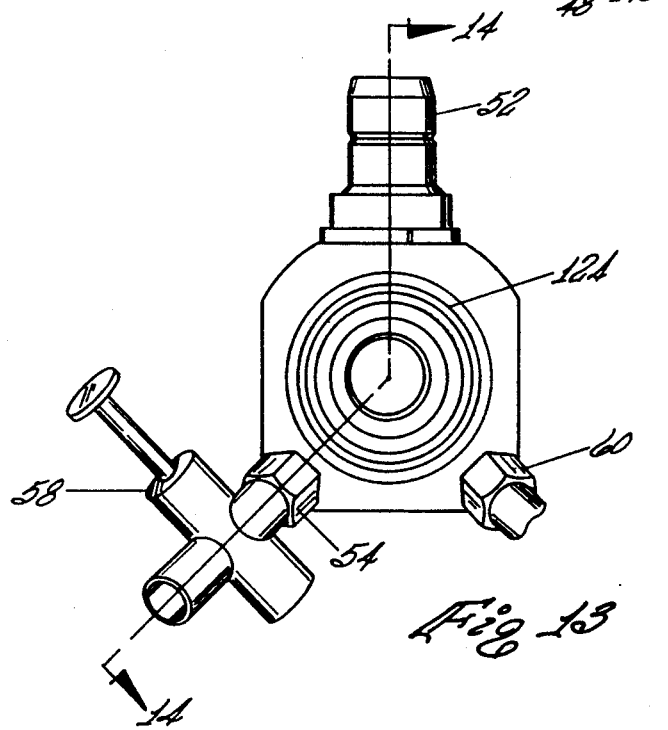
FIG. 13 is a partial proximal end elevational view showing the extended housing and one trumpet valve operatively connected to the means for defining an opening which is operatively connected to the fluid flow channel to conduct pressurized fluid flow to the nozzle located at the distal end of the laparoscope.

FIG. 13 shows a partial proximal end elevational view of the assembly illustrated in FIG. 14 and shows in greater detail that the light post 52 extends in a substantially normal direction from the extension member 48. The upper portion 124 of the extension member 48 is adapted to be operatively connected to an eyepiece as described hereinbefore. The means for defining an output or port 60 and the means for defining an output or port 54 are adapted to be operatively connected to a valving means. In FIGS. 13 and 14, the preferred means for defining valving means is a trumpet valve 58. However, it is envisioned that any type of valving means could be used such as, for example, a stop cock valve.

FIG. 14 illustrates in greater detail the use of an image transferring means 130 which is located within the rigid elongated sheath tube 32. As depicted in FIG. 13, the distal section 36 includes a fluid flow channel 140 which terminates in the nozzle 80. The fluid flow channel 140 includes a proximal section 146 which extends through the extension member 48 and into an operative connection with the means for defining an outlet or port 54. Port 54 is operatively connected to the extension member 48 through any known connecting means such as, for example, a threaded connecting means. In the preferred embodiment, a trumpet valve fluid control means 58 is fastened to port 54.

The light post 52 supports the fiber optic light guide elements 120 which is then interspersed within the space existing between the exterior surface of the image transferring means channel 142 and the inner surface of the rigid elongated sheath tube 32.

The proximal end 148 of the image transferring means channel 142 communicates with the portion of the extension member 48 as depicted in FIG. 13.

Referring now to FIGS. 15 and 16, these figures depict a subassembly comprising the image transferring means channel 142 and the fluid flow channel 140 including deflected proximal section 146. The proximal end 148 of the image transferring means channel 142 is adapted to be operatively inserted into and through the extension member 48 as illustrated in FIG. 14. Support and positioning members 150 appear as fins which are equidistantly spaced around the periphery of channel 142 and positioning members 146 are used for positioning the channel 142 in a proper spaced relationship with the rigid elongated sheath tube 32 and provides means for defining space 70 described hereinbefore.

FIG. 17 illustrates pictorially the design of the nozzle 80 of the preferred embodiment. The nozzle 80 includes a deflecting head 170 which includes a dispensing slot 172 for shaping the width and thickness of the fluid flow to be directed across the transparent member 76. In the preferred embodiment, the angle of the fluid flow between dash lines 162 is in the order of about 90°. However the width of the spray, which takes on a wedge shape during the spraying operative, can be selected by a person skilled in the art depending upon the specific application and the size of the transparent member 76.

FIG. 18 shows in greater detail, the relationship between the distal end of the laparoscope 44, the fluid flow channel 140 and the nozzle 80. The nozzle 80 has its deflecting head 170 extending or protruding slightly therefrom and positioning the dispensing slot 172 so as to be able to direct the spray across the transparent member 76 as depicted in FIG. 17. The nozzle 80 includes a channel 176 which conducts fluid flow from the fluid flow channel 140 through the head 170 and into communication with the dispensing slot 172.

Figure 19:
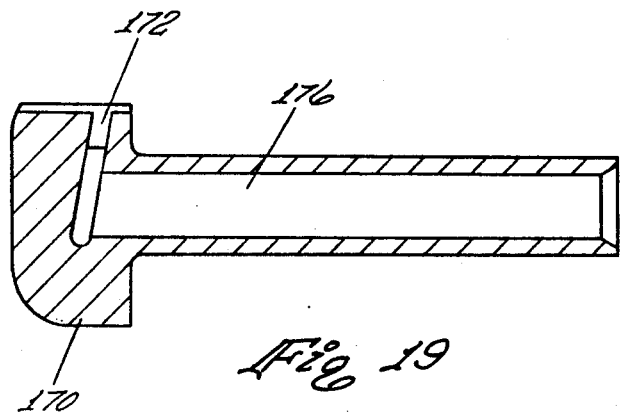
FIG. 19 is a partial side cross-sectional view showing the preferred embodiment of a structure of the nozzle for producing a shaped discharge from the nozzle.
Figure 20:
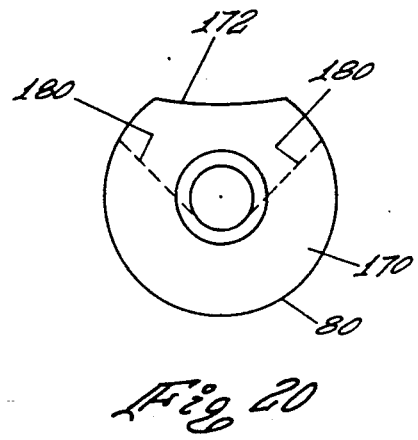
FIG. 20 is a proximal end elevational view of the nozzle of FIG. 19.

FIGS. 19 and 20 show in greater detail, the structure of the preferred embodiment of the nozzle 80 for practicing the invention. The nozzle shows the relationship between the head 170, the dispensing slot 172 and a channel 176 for directing the fluid flow into the orifice 172. In the preferred embodiment, the fluid is introduced into the channel at a pressure of approximately 300 mm of Hg above atmosphere and the sizing of the channel 176 and the dispensing slot ;72 are selected so as to dispense the fluid under pressure and with an appropriate fluid flow to effectively remove impeding agents from the exterior surface of the image passing means.

In FIG. 20, the dispensing slot 172 is shown to have sloping walls depicted by dash lines 180. The position of the sloping walls shown by dashed lines 180 together with the width of the slot 172 determines the characteristics and shape of the fluid flow.

Figure 21:
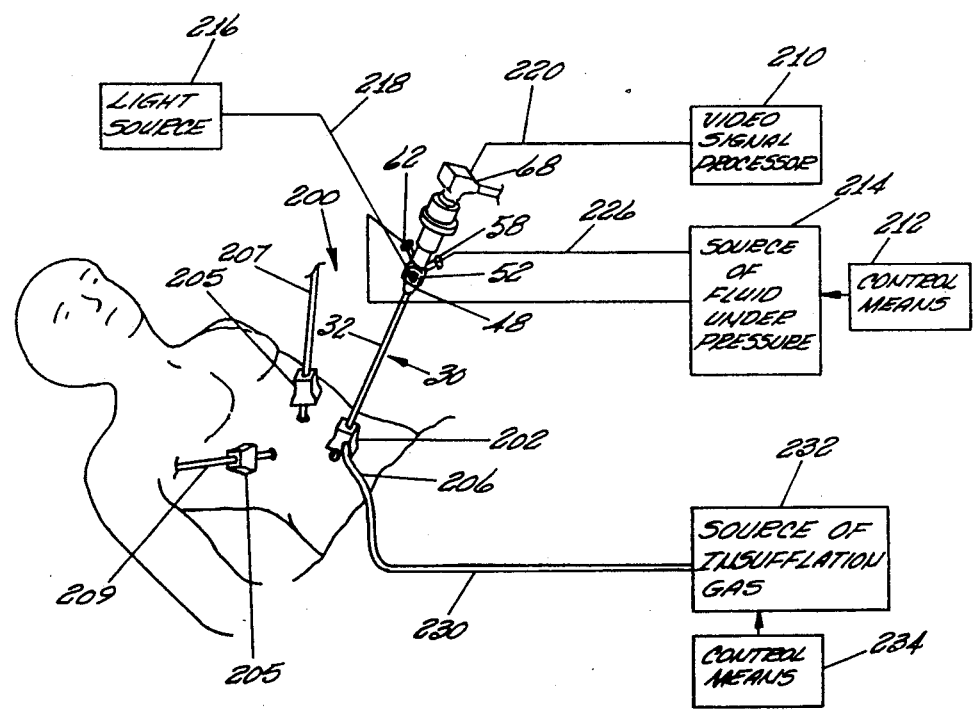
FIG. 21 is a pictorial representation of a system which includes a laparoscope subject of the present invention for practicing a method for performing laparoscopic procedures and a system therefor.

FIG. 21 depicts a system for performing a laparoscopic procedure and a method for performing a procedure in a cavity.

The method for performing a procedure within a cavity comprises the step of providing a laparoscope 30 including a rigid elongated sheath tube 32 having a selected length, a distal section and a proximal section. The distal section includes means for defining a distal tip including a fluid tight transparent member capable of passing images as described hereinbefore. The transparent member has an exterior surface located at the distal tip. The laparoscope includes means for defining, at the distal tip, means for directing a fluid flow across the exterior surface of the transparent member to remove therefrom image impeding agents. The laparoscope used in the above step includes the means for directing the fluid flow across the exterior surface of the transparent member to remove therefrom image impeding agents, the step of applying fluid under a predetermined pressure through the fluid flow directing means is performed to remove any image impeding means from the exterior surface of the transparent member. Thus, when the laparoscope 30 is inserted into the peritoneal cavity as illustrated in FIG. 21, applying the fluid under a predetermined pressure is utilized to remove such material as fog or organic material directly from the exterior surface. After the step of applying fluid is performed, the next step is the viewing from the proximal section of the rigid elongated sheath tube of the cavity through the transparent member in the laparoscope. As illustrated in FIG. 21, the method further includes the use of smaller cannula and trocar assemblies 205 to receive working accessories or tools shown as elements 207 and 209. The working tools could be an atraumatic forceps or similar tool. The working tools 207 and 209 are passed through the cannula and trocar assemblies 205 into the peritoneal cavity to perform the surgical procedure such as, for example, to perform the removal of the gallbladder.

As illustrated in FIG. 21, the method also includes applying fluid under a predetermined pressure through the irrigation channel which has its opening at port 62. In the embodiment FIG. 21, the source of fluid could be an intravenous ("IV") bag of saline solution which has a blood pressure cuff wrapped around wherein the pressure of the blood pressure cuff is pumped up to about 300 mm of Hg. The fluid is then passed from the intravenous bag, under pressure, through the intravenous tubing 226 and 228 to the laparoscope. The saline solution is utilized for forming the fluid flow and irrigation flow to be used by the surgeon during the procedure to wash the viewing window and to irrigate the operating site.

In the alternative, the irrigation channel can be operatively connected to a high pressure fluid flow device, such as, for example, Karl Storz brand Nezhat-Dorsey hydro-dissection pump which produces pressure from 0 to 775 mm of Hg which is used for hydro-dissection of tissue under direct observation of the laparoscope 30. For hydro-dissection, a higher pressure could be used depending on the procedure.

The use of a peristaltic pump to deliver the fluid for either the irrigation flow or hydro-dissention flow is preferred because of the cleansing action that is developed due to the characteristics of the pulsating fluid flow from such a pump.

The laparoscope 30 illustrated in FIG. 21 includes a video camera means 68 which is operatively connected to a video signal processor 210 through cable 220. Typically, the video signal processor includes a monitor which is observed by the surgeon during the procedure. Thus, the laparoscopic procedure is generally observed or performed by use of a video image, rather than through the eyepiece.

In addition, the method for performing a procedure in the cavity using a laparoscope having the structure illustrated in FIG. 7, provides the surgeon with a working channel which could be used during the procedure. Specifically, the method would include the step of passing a working accessory or tool through the working channel to perform the procedure in the cavity can be utilized. The instruments that are available that can be used through the working channel include coagulating probes, bipolar probes and other similar devices.

Lastly, when the surgeon has completed the surgical process, the laparoscope is then removed from the cavity by withdrawing the same through the cannula and trocar assembly 202.

In addition, a system for performing laparoscopic procedures is shown in FIG. 21. The system includes a laparoscope having the structures described herein. Of importance, is that the laparoscope includes means for defining a nozzle for directing a fluid flow across the exterior surface of the distal lens to remove image impeding agents therefrom. In the laparoscope 30 illustrated in FIG. 21, the laparoscope includes means for defining at the proximal end, an opening or port 54 which is adapted to be operatively connected to a source of pressurized fluid. In addition, the laparoscope includes means for defining an image transferring means, a means for defining a fiber optic light guide means, both of which extend from the distal tip to the proximal end of the rigid elongated sheath tube.

In the system depicted in FIG. 21, a primary cannula and trocar assembly 202 which is provided for forming an opening in the peritoneal cavity and include means for passing the distal section of the laparoscope 30 into the peritoneal cavity. The cannula and trocar assembly 202 include means 206 for passing an insufflator gas therethrough into the peritoneal cavity to insufflate the same. The system further includes a means for defining a source of insufflation gas 232 which is under a control means 234 to regulate the flow rate and pressure of the insufflation gas. The insufflation gas is applied from the source of gas 232 through conduit 230 to the means for passing the insufflator gas 206 located on the cannula and trocar assembly 202.

As illustrated in the system in FIG. 21, a means including a video camera 68 and a video signal processing means 210 is operatively connected to the proximal end of the laparoscope 30 for processing video images of the laparoscopic procedures transmitted through by the image transferring means. The video signal processing means 210 could include a video monitor, VCR, video printer or the like. A light source 216 is operatively connected by a light transmitting cable 218 to the fiber optic light guide means through light post 52 at the proximal end of the laparoscope and provides illumination of the operating site to generate the optical image which is passed through the transparent member, through the image transferring means to the proximal end of the laparoscope 30 where the same is converted into a video image as described hereinbefore.

In addition, a source of fluid under pressure 214, Which may be controlled by a control means 212, is operatively connected by a tubing 226 and 228 to the trumpet valves 58 and 62 for selectively applying fluid under pressure to at least one of the channels in the laparoscope to selectively direct a fluid flow through a nozzle and across the exterior surface of the transparent member or, alternatively, to the second channel to produce a fluid flow which extends generally along an axial path which is directed primarily parallel to the elongated axis of the laparoscope.

Figure 22:
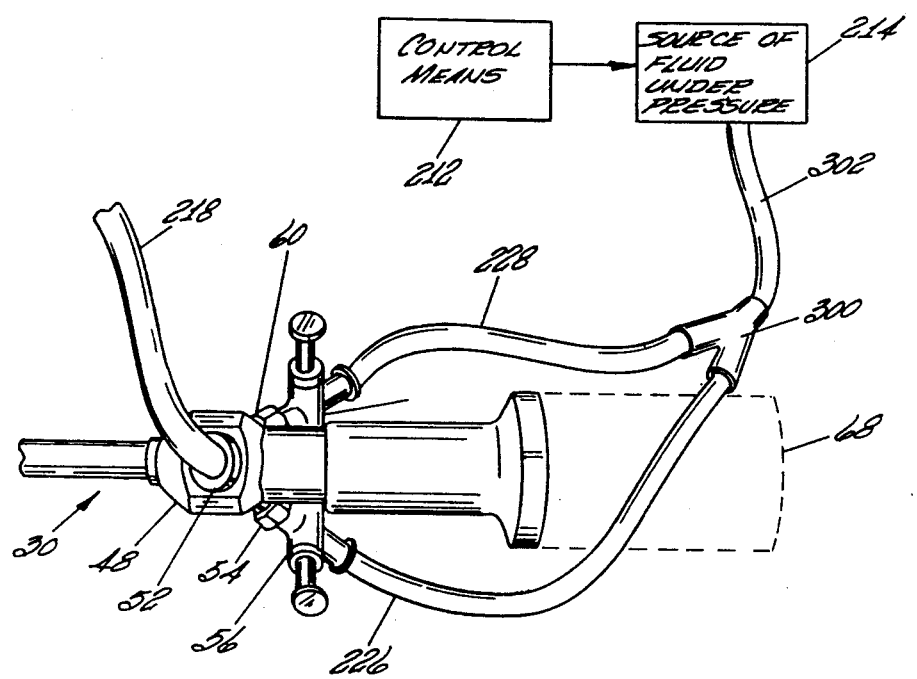
FIG. 22 is a partial representation of one structure of a valve means which permits fluid flow to be selectively applied to the distally located nozzle and irrigational orifice.
Figure 23:
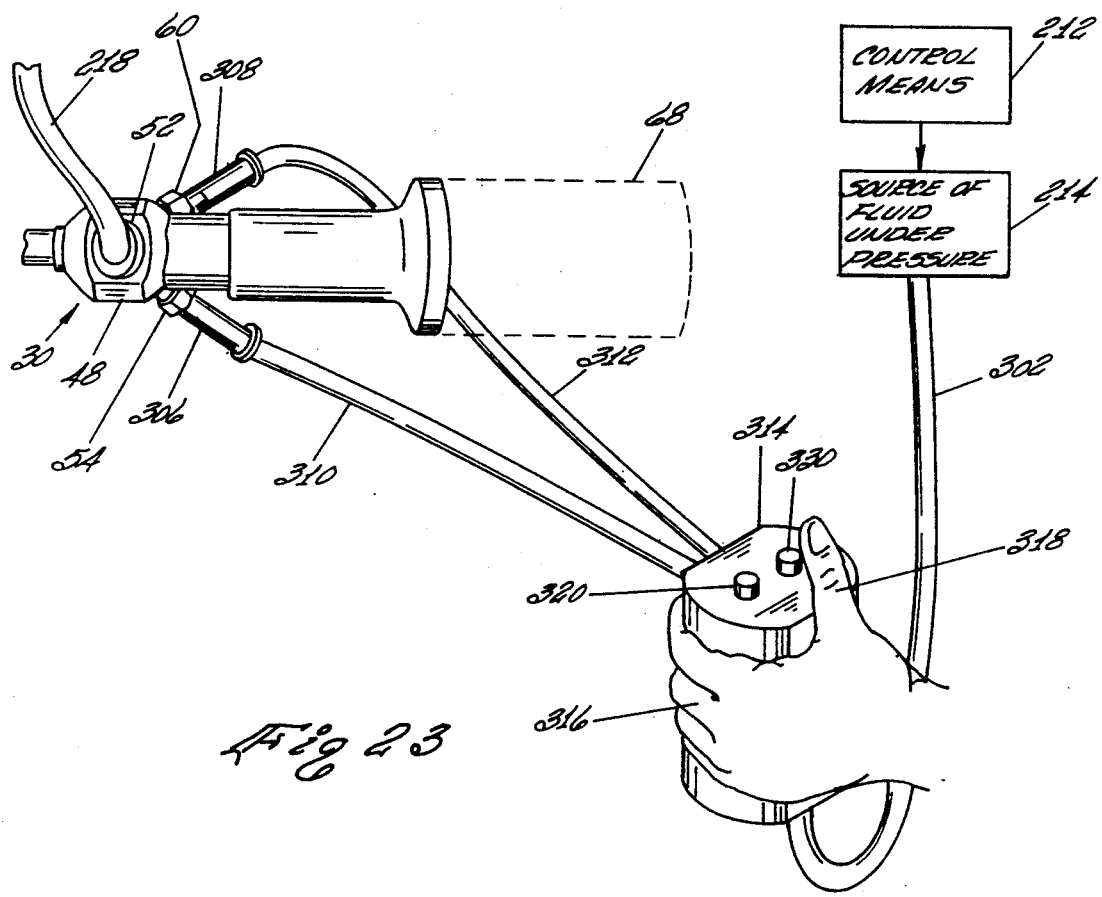
FIG. 23 is pictorial representation of another embodiment wherein a manually actuatable valve control means is operatively connected between a source of pressurized fluid and the laparoscope of the present invention.

FIG. 22 and 23 depict two alternative laparoscope structures for practicing the method and the procedure of FIG. 21. In FIG. 22, the laparoscope 30 is illustrated to have the extension member 48 having the light cable 218 connected to the light post 52. The ports 54 and 60 are operatively connected to trumpet valves 58 and 62 respectfully. The trumpet valves 58 and 62 are operatively connected to tubing 226 and 228 respectfully which are operatively connected to a "Y" shaped member 300. The "Y" shaped member 300 is operatively connected to a tubing 302 to a source of fluid under pressure 214. The source of fluid under pressure can be controlled by a control means 212. In operation, the source of fluid under pressure passes a fluid such as, for example, a saline solution under a pressure of approximately 300 mm of Hg to the "Y" shaped member 300 where the fluid under pressure is applied concurrently through tubing 226 and 228 to the trumpet valves 58 and 62. During a procedure, the surgeon, by use of a thumb or finger, can depress either of the trumpet valves which would permit the fluid to be passed under pressure to the nozzle or irrigation orifice, as the case may be. For example, if the surgeon actuated trumpet valve 58, a fluid flow under pressure would pass through the fluid flow channel to the nozzle 80 (as depicted in FIGS. 4 through 8) to direct a fluid flow across the exterior surface of the transparent member to remove image impeding agents therefrom. Also, if the surgeon desires to have an irrigation flow, the surgeon can actuate trumpet valve 62 which would cause an irrigation flow to be dispensed through opening 86 as depicted in FIGS. 4 through 8.

FIG. 23 shows an alternate structure wherein the trumpet valves are eliminated and are replaced with straight tube connections, shown generally as 306 and 308. In the embodiment of FIG. 22, the straight tube connectors 306 and 308 are operatively connected to tubing members 310 and 312 respectively which, in turn, are operatively connected to a button actuatable valve means shown generally as 314. The button actuatable valve means 314 is operatively connected through a tubing 302 to the source of fluid under pressure 214 which is controlled by a control means 212.

In operation, the source of fluid under pressure 214 applies fluid through conduit 302 to the valve actuatable control means 314. The user places the user's hand, depicted by 316, around the button actuatable valve means 314 and by use of the thumb 318 can selectively depress either of the valves 320 or 330. If valve 320 is depressed, then the fluid flow under pressure is passed through tubing 310 through straight tube connector 306 through port 54 and to the fluid flow channel into the nozzle 80 as depicted in FIGS. 4 through 8. In the alternative, if the surgeon depresses button 330, fluid is permitted to pass into tubing 312 and through straight tube connector 308 into port 60 and then through the first channel to the irrigation orifice to develop the irrigation flow which provides irrigation at the operative site to remove debris therefrom. By being able to remove debris from the operating site or washing of the window during the procedure, the surgeon can then have a clear optical image of the operative site.

In the alternative, the control means 212 of the fluid source 214 could be a high pressure source which could be directly connected to port 62 and through the irrigation channel to the irrigation orifice. The surgeon could actuate the trumpet valve to develop a high pressure fluid flow to perform hydro-dissection of tissue during the procedure.

The laparoscope, method and system described herein have applications for performing a wide variety of surgical procedures. Although the preferred embodiment includes use of a laparoscope which is adapted for performing surgical procedures in the peritoneal cavity, it is readily apparent that the laparoscope and its associated components could be utilized for performing procedures within other body cavities. Also, the laparoscope has specific applications for performing a laparoscopic cholecystectomy that is for removing the gallbladder. However, it is envisioned that the same system, method and apparatus could be utilized for removing other organs, such as, for example, the appendix and kidney, or to excise tissue, to remove portions of the liver or other organs or tissue located within the peritoneal cavity.

Also, the laparoscope could be used as a boroscope in industrial or other applications for inspecting and performing procedures in a cavity such as, for example, in a jet engine.

The source of fluid can be a wide variety of sources and can be other than a saline solution. The pressure flow rates and pressures desired for hydro-dissection is a function of the design characteristics of the system.

Also, the irrigation channel could be utilized for other functions, such as for passing small working tools, suction, or other procedures. Also, as illustrated in FIG. 7, the center line of the image transferring means channel, can be offset to the elongated axis of the rigid elongated sheath tube to provide the enlarged space to receive a larger accessory channel. It is envisioned that further offsets could be obtained by moving the image transferring means channel to be contiguous to the inside surface of the rigid elongated sheath tube which would make the enlarged space larger. The space could then accommodate a larger accessory channel. A trade off exists since a reduced number of fiber optic elements of the fiber light guide means would exist on one side of the distal end, which could degrade the optical image on one side. Also, more than three channels could be provided in the space provided between the exterior surface of the image transferring means channel and the inside interior surface of the rigid elongated sheath tube. The channels could be positioned at any angle relative each other and the embodiment is depicted in FIGS. 4 through 8 are only typical of the various structure arrangements that could be utilized in a laparoscope for practicing this invention.

What is claimed is:

1. An instrument comprising
   a rigid elongated sheath tube having interior side walls, a selected length and a distal end, said distal end including means for passing an image, said image passing means having an exterior surface located at said distal end;
   means located within said rigid elongated sheath tube for defining at said distal end means for directing a fluid flow across the exterior surface of said image passing means to remove therefrom image impending means;
   said image passing means and fluid directing means being positioned within said rigid elongated sheath tube to define spaces between said interior side walls, said image passing means and said fluid directing means; and
   means located within said rigid elongated sheath tube for defining fiber optic elements which are distributed within said spaces and around the exterior surface for forming a light guide to illuminate an operative site.

2. A laparoscope comprising
   a rigid elongated sheath tube having interior side walls, a selected length and a distal section, said distal section having a means for defining a distal tip including fluid tight, transparent member capable of passing an optical image, said transparent member having an exterior surface located at said distal tip;

means located within said rigid elongated sheath tube for defining at said distal tip a nozzle for directing a fluid flow across the exterior surface of said transparent member to remove therefrom optical image impeding agents;

said image passing means and fluid directing means being positioned within said rigid elongated sheath tube to define spaces between said interior side walls, said image passing means and said fluid directing means; and means located within said rigid elongated sheath tube for defining fiber optic elements which are distributed within said spaces and around the exterior surface for forming a light guide to illuminate an operative site.

3. The laparoscope of claim 2 wherein said distal tip terminates in a generally rounded cross-section.

4. The laparoscope of claim 2 wherein said distal tip of said rigid elongated sheath tube includes means defining a proximal end and further includes means defining a first channel which extends axially from the proximal end of the rigid elongated sheath tube to the distal tip thereof, said first channel being operatively coupled to said means defining said nozzle.

5. The laparoscope of claim 4 wherein said first channel includes a means defining at its proximal end an opening which is adapted to be operatively connected to a source of fluid.

6. The laparoscope of claim 5 wherein said means defining an opening is operatively connected to a valve means for selectively applying fluid from the source of fluid through said first channel to said nozzle to produce a fluid flow across the exterior surface of said transparent member.

7. The laparoscope of claim 6 wherein the source of fluid is under a predetermined pressure.

8. The laparoscope of claim 6 wherein said fluid is a saline solution which is under a pressure in the order of about 300 mm of Hg.

9. The laparoscope of claim 6 wherein said valve means is a manually controlled valve.

10. The laparoscope of claim 6 wherein said valve means is a trumpet valve.

11. The laparoscope of claim 4 wherein said rigid elongated sheath tube further includes means defining an image transferring means channel which is adapted to receive an image transferring means, said image transferring means channel having its distal end positioned adjacent said transparent member.

12. The laparoscope of claim 11 wherein said rigid elongated sheath tube has an elongated axis and said image transferring means channel has a central axis.

13. The laparoscope of claim 11 wherein the elongated axis of said rigid elongated sheath tube is coaxial with the central axis of the said image transferring means channel.

14. The laparoscope of claim 11 wherein said central axis of the image transferring means channel is offset from the elongated axis of said rigid elongated sheath tube.

15. The laparoscope of claim 11 wherein the rigid elongated sheath tube further includes an image transferring means located within the image transferring means channel.

16. The laparoscope of claim 4 wherein the rigid elongated sheath tube has an elongated axis and includes means defining a second channel which extends axially from the proximal end of the rigid elongated sheath tube to the distal tip thereof; and means operatively coupled to said second channel for defining an orifice for directing a stream of fluid along a path which is substantially in alignment with the direction of view of said image transferring means.

17. The laparoscope of claim 16 wherein the rigid elongated sheath tube further includes means for defining a fiber optic light carrying means located internally within said rigid elongated sheath tube and which is interspersed around said first channel, said second channel and between said image transferring means channel and rigid elongated sheath tube and which extends from the proximal end of the rigid elongated sheath tube to the distal tip thereof.

18. The laparoscope of claim 16 wherein the size of the first channel and second channel are the same.

19. The laparoscope of claim 16 wherein the size of the second channel is greater than that of the first channel.

20. The laparoscope of claim 19 wherein the interior dimension of the first channel is approximately 1 millimeter and the interior dimension of the second channel is approximately 2 millimeters.

21. The laparoscope of claim 19 wherein the exterior dimension of the rigid elongated sheath tube is approximately 10 millimeters.

22. The laparoscope of claim 20 wherein the selected length is between about 150 millimeters to about 350 millimeters.

23. The laparoscope of claim 22 wherein the selected length is about 300 millimeters.

24. The laparoscope of claim 15 wherein the outside dimension of the image transferring means channel is about 6.5 millimeters.

25. The laparoscope of claim wherein the laparoscope includes an optical wedge located distal to the objective lens system to provide a deviated direction of view having an angle of about 0 degrees to about 30 degrees when viewing in $CO_2$.

26. The laparoscope of claim 16 wherein said rigid elongated sheath includes means for defining at least one working channel;
means defining interior walls in said at least one working channel; and
means for coating the interior walls of said at least one working channel with material having a reduced coefficient of friction to facilitate passage of accessories through the at least one working channel.

27. The laparoscope of claim 16 wherein said second channel includes a means defining an opening which is adapted to be operatively coupled to a pressurized source of fluid.

28. The laparoscope of claim 27 wherein said rigid elongated sheath tube includes means for defining an orifice at the distal end of the second channel which is capable of directing a pressurized stream of fluid along an axis parallel to the elongated axis of said rigid elongated sheath tube.

29. The laparoscope of claim 26 wherein said rigid elongated sheath includes means for defining at least one working channel; and
means including an elongated tube operatively connected to said at least one working channel for extending said elongated tube beyond the distal tip of said laparoscope.

30. The laparoscope of claim 16 wherein said rigid elongated sheath includes
means for defining at least one working channel; and
a laser guide operatively positioned within said at least one working channel, said laser guide being movable within said at least one channel to extend beyond the distal tip of said laparoscope.

31. A laparoscope for performing laparoscopic surgery comprising
a rigid elongated sheath tube having interior side walls, an elongated axis, a selected length, a distal section and a proximal section with terminates in a proximal end, said distal section having a means for defining a distal tip including fluid tight image passing means, said image passing means having an exterior surface located at said distal tip;
said image passing means and fluid directing means being positioned within said rigid elongated sheath tube to define spaces between said interior side walls, said image passing means and said fluid directing means;
means located within said rigid elongated sheath tube for defining fiber optic elements which are distributed within said spaces and around the exterior surface for forming a light guide to illuminate an operative site;
means located within said rigid elongated sheath tube for defining at said distal tip a nozzle for directing a fluid flow across the exterior surface of said image passing means to remove therefrom image impending agents;
means defining a first channel which extends axially from the proximal end of the rigid elongated sheath tube to the distal tip thereof, said first channel being operatively coupled to said means defining at said nozzle, said first channel including means for defining the proximal end an opening which is adapted to be operatively connected to a source of pressurized fluid; and
means defining a second channel which extends axially from the proximal end of the rigid elongated sheath tube to the distal tip thereof.

32. The laparoscope of claim 31 further comprising
means operatively coupled to said second channel at the distal tip of said laparoscope for defining an orifice for directing a stream of fluid along a path which is substantially in alignment with the direction of view of said image transferring means.

33. The laparoscope of claim 31 further comprising
means operatively coupled to said second channel at the distal tip of said laparoscope for defining a second nozzle for directing a fluid flow across the exterior surface of said image passing means.

34. The laparoscope of claim 31 further comprising
means operatively coupled to the proximal end of said second channel for applying a source of vacuum thereto.

35. The laparoscope of claim 31 wherein said rigid elongated sheath tube further includes
means defining an image transferring means channel having a central axis which is adapted to receive an image transferring means, said image transferring means channel having its distal end positioned adjacent said image passing means.

36. The laparoscope of claim 35 wherein the rigid elongated sheath tube further includes
an image transferring means located within the image transferring means channel.

37. The laparoscope of claim 35 wherein the elongated axis of the rigid elongated sheath tube is coaxial with the central axis of said image transferring means.

38. The laparoscope of claim 35 wherein the central axis of the image transferring means channel is offset from the elongated axis of said rigid elongated sheath tube defining a passageway having a known width between one side of the image transferring means and the rigid elongated sheath tube.

39. The laparoscope of claim 38 wherein said rigid elongated sheath tube further comprises
means defining a working channel located within said passageway for passage of accessories therein.

40. The laparoscope of claim 38 wherein said rigid elongated sheath tube includes means defining a third channel and a fourth channel for performing a procedure at a working area within a cavity.

41. The laparoscope of claim 40 wherein said first channel, said second channel, said third channel and said fourth channel are positioned at selected angular positions to each other.

42. The laparoscope of claim 41 wherein selected angle position of each adjacent channel is approximately 90°.

43. The laparoscope of claim 39 wherein the size of said working channel is greater than the size of said second channel.

44. The laparoscope of claim 39 wherein the rigid elongated sheath tube further includes
means for defining a fiber optic light carrying means located internally within said rigid elongated sheath tube and which is interspersed around said first channel, said second channel, said third channel and between said image transferring means channel and rigid elongated sheath tube and which extends from the proximal end of the rigid elongated sheath tube to the distal tip thereof.

45. The laparoscope of claim 31 wherein the proximal end of said first channel includes means defining an opening which is adapted to be operatively connected to a source of fluid under pressure.

46. The laparoscope of claim 45 wherein said opening means is operatively connected to a valve means for selectively applying fluid from the source of fluid under pressure to said nozzle to produce a fluid flow across the exterior surface of said distal lens.

47. The laparoscope of claim 46 wherein the source of fluid is saline solution having a predetermined pressure.

48. The laparoscope of claim 47 wherein said fluid pressure is in the order of about 200 mm of Hg to about 350 mm of Hg.

49. The laparoscope of claim 46 wherein said valve means is a manually controlled valve.

50. The laparoscope of claim 46 wherein said valve means is a trumpet valve.

51. A method for performing a procedure in a cavity comprising the steps of
providing a laparoscope including a rigid elongated sheath tube having interior side walls, a selected length, a distal section and a proximal section, said distal section including a means for defining a distal tip including a fluid tight, transparent member capable of passing an image, said transparent member having an exterior surface located at said distal tip, said image passing means and fluid directing means being positioned within said rigid elongated sheath tube to define spaces between said interior side walls, said image passing means and said fluid directing means, means located within said rigid elongated sheath tube for defining fiber optic elements which are distributed within said spaces and around the exterior surface for forming a light guide to illuminate an operative site and a means for defining at said distal tip means for directing a fluid flow across the exterior surface of said transparent member to remove therefrom image impeding agents;

applying fluid under a predetermined pressure through the fluid flow directing means to remove image impeding means from the exterior surface of the transparent member; and viewing from the proximal section of the rigid elongated sheath tube said cavity through said transparent member in the laparoscope.

52. The method of claim 51 wherein the means for defining this fluid through a nozzle and the transparent member is a distal lens and the step of applying fluid under pressure includes directing the fluid through a nozzle across the exterior surface cf the transparent member to remove the image impeding agents from the exterior surface of said distal lens.

53. The method of claim 51 wherein the step of applying fluid under pressure includes means for directing a fluid flow of saline under a pressure of about 200 mm of Hg to about 350 mm of Hg.

54. The method of claim 52 wherein the laparoscope further includes a second channel and a working channel and further comprises the step of
passing a working tool through at least one of said second channel and working channel to perform a procedure in said cavity.

55. The method of claim 54 further comprising the step of
using the other of said second channel and working channel to perform a separate procedure in said cavity.

56. The method of claim 51 further comprising the step of with drawing the laparoscope from the cavity.

57. A system for performing laparoscopic procedures comprising
a laparoscope comprising
a rigid elongated sheath tube having interior side walls, an elongated axis, a distal section and a proximal section which terminates in a proximal end, said distal section having a means for defining a distal tip including fluid tight distal lens, said distal lens having an exterior surface located at said distal tip;

means for defining an image transferring means which extends from the distal tip to the proximal end of the rigid elongated sheath tube;

said image passing means and fluid directing means being positioned within said rigid elongated sheath tube to define spaces between said interior side walls, said image passing means and said fluid directing means;

means located within said rigid elongated sheath tube for defining fiber optic elements which are distributed within said spaces and around the exterior surface for forming a light guide to illuminate an operative site;

means located within said rigid elongated sheath tube for defining at said distal tip a nozzle for directing a fluid flow across the exterior surface of said distal lens to remove therefrom optical image impeding agents;

means defining a first channel which extends axially from the proximal end of the rigid elongated sheath tube to the distal tip thereof, said first channel being operatively coupled to said means defining said nozzle, said first channel including means for defining the proximal end an opening which is adapted to be operatively connected to a source of pressurized fluid;

means for defining a second channel which extends axially from the proximal end of the right elongated sheath tube to the distal tip thereof;

means for defining an orifice for directing a stream of fluid along a path which is substantially in alignment with the direction of view of said image transferring means;

a cannula and trocar assembly for forming an opening in the peritoneal cavity and including means for passing the distal section of the laparoscope into the peritoneal cavity, said annular and trocar assembly including means for passing an insufflator gas therethrough into the peritoneal cavity to insufflate the same;

means defining a source of insufflation gas and means for regulating the flow rate and pressure of the insufflation gas operatively connected to means for passing the insufflation gas;

means including a video camera and video signal processing means operatively coupled to the proximal end of the laparoscope for processing a video image of the laparoscopy procedures;

a light source operatively connected to the fiber optic light guide means at the proximal end of the laparoscope; and means including a source of fluid under pressure operatively connected to the proximal end of the laparoscope for selectively applying fluid under pressure to at least one of said first channel to direct a fluid flow across the exterior surface of the transparent member and said second channel to produce an irrigating fluid along a path substantially parallel to the direction of view of the laparoscope.

* * * * *